United States Patent [19]
Reddy et al.

[11] Patent Number: 5,287,060
[45] Date of Patent: Feb. 15, 1994

[54] IN-TANK CONDUCTIVITY SENSOR

[75] Inventors: Vilambi N. Reddy, Lakewood; Bruce M. Eliash, Los Angeles; Frank A. Ludwig, Rancho Palos Verdes; Nguyet H. Phan, Los Angeles, all of Calif.

[73] Assignee: Hughes Aircraft Company, Los Angeles, Calif.

[21] Appl. No.: 977,389

[22] Filed: Nov. 17, 1992

[51] Int. Cl.$^5$ ............................................. G01N 33/18
[52] U.S. Cl. ..................... 324/439; 324/450; 324/447; 422/110; 204/229; 204/225; 204/238
[58] Field of Search ............... 422/110; 204/229, 237, 204/238, 239, 225; 324/439, 438, 450

[56] References Cited

U.S. PATENT DOCUMENTS

| | | | |
|---|---|---|---|
| 4,087,743 | 5/1978 | Bressan | 324/439 |
| 4,803,869 | 2/1989 | Barcelona | 324/439 |
| 4,871,427 | 10/1989 | Kolesar | 324/439 |
| 4,988,948 | 1/1991 | Francard | 324/439 |

Primary Examiner—Kenneth A. Wieder
Assistant Examiner—Jose M. Solis
Attorney, Agent, or Firm—M. E. Lachman; M. W. Sales; W. K. Denson-Low

[57] ABSTRACT

A conductivity sensor adapted for use in the conductimetric analysis of liquids includes a pair of conductivity electrodes incorporated into a conductivity cell assembly having a liquid flow control chamber, sensing chamber, and liquid exit chamber. Liquids to be measured are pumped into the liquid flow control chamber, where any turbulence in the liquid is dampened. The non-turbulent liquid is passed from the liquid flow control chamber to the sensing chamber, where the conductivity of the liquid is determined. The sensing chamber is adapted for changing the height of a column of liquid between the pair of conductivity electrodes in order to vary the cell constant of the sensor. The non-turbulent liquid is passed from the sensing chamber to the liquid exit chamber, where it exits the sensor. The sensor is well-suited for use in measuring conductivities of plating bath solutions and monitoring concentrations of major constituents of plating bath solutions.

23 Claims, 3 Drawing Sheets

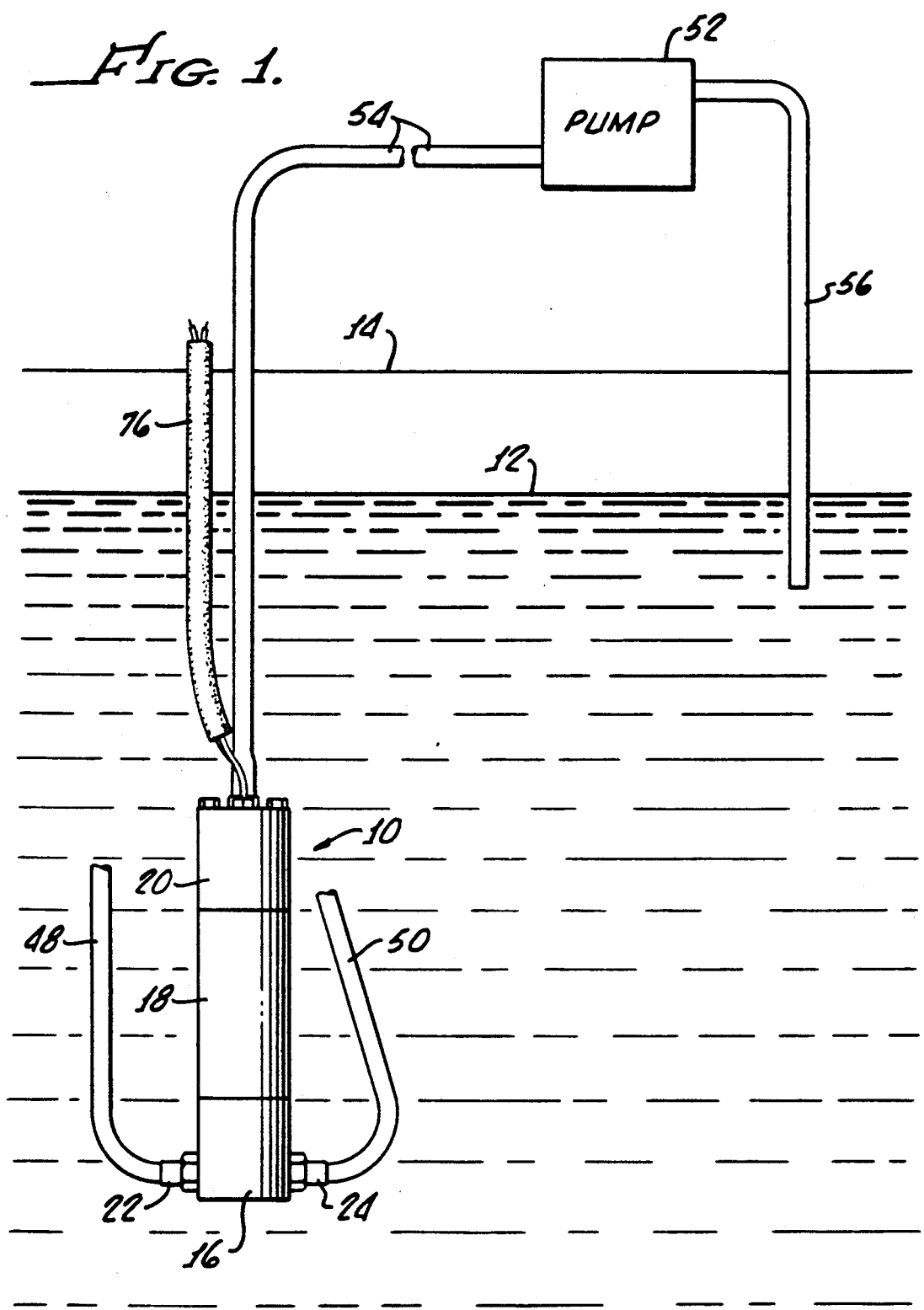

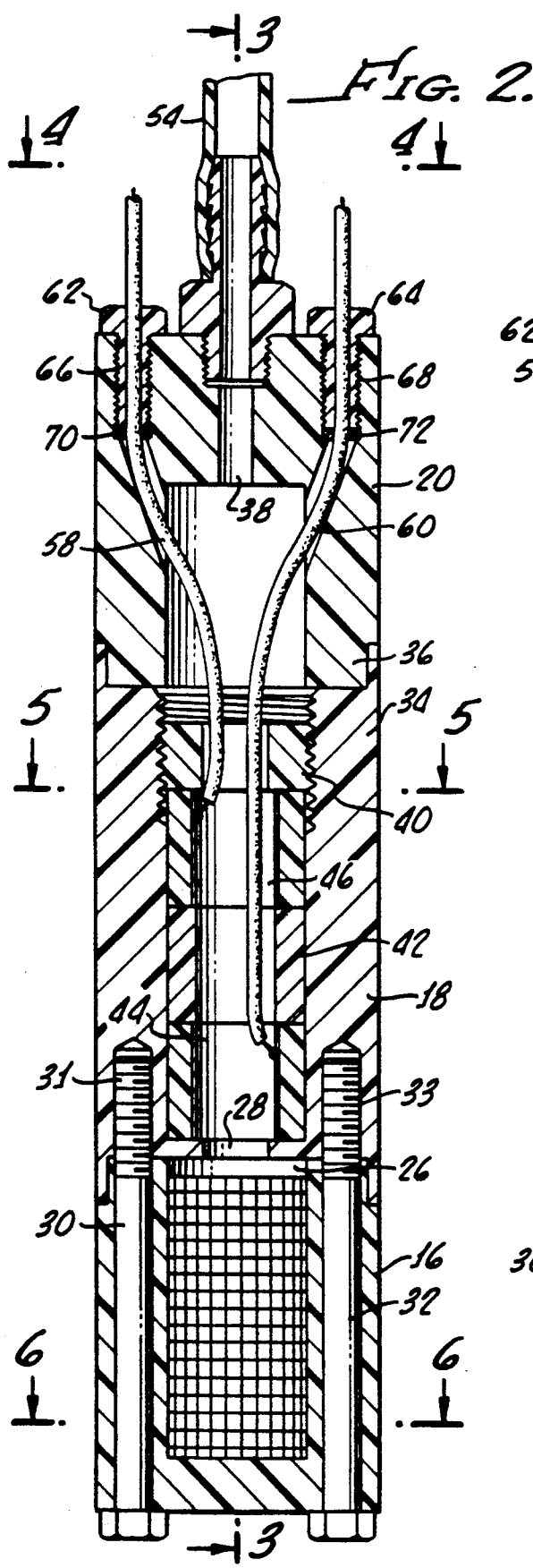
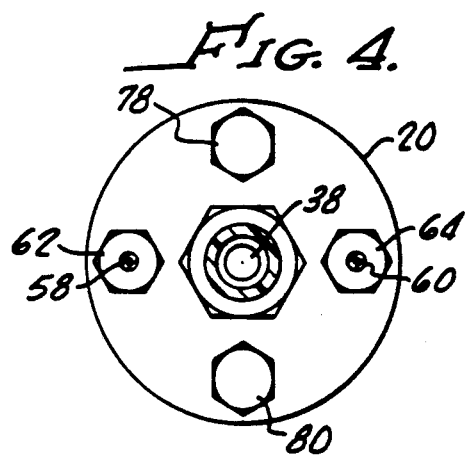
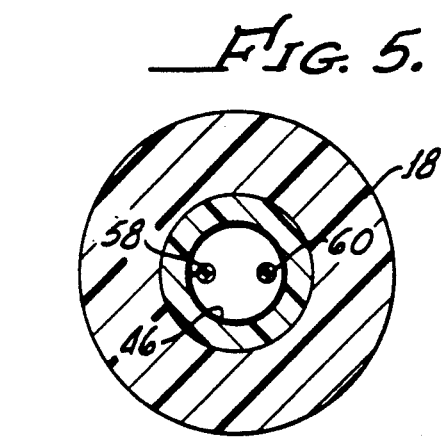
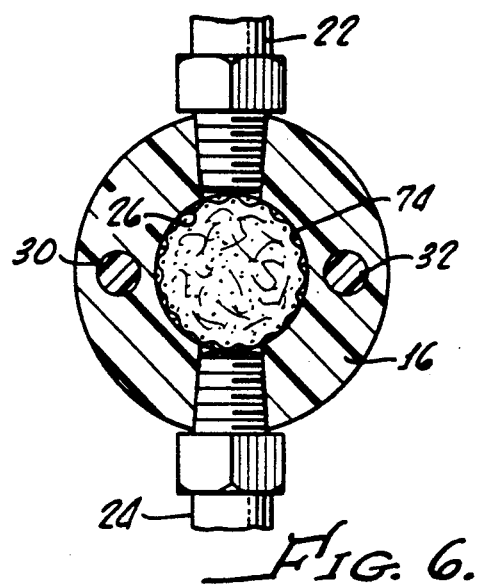

IN-TANK CONDUCTIVITY SENSOR

BACKGROUND OF THE INVENTION

1. Field of the Invention

The present invention relates generally to electrochemical conductivity sensors which are designed for use in measuring and monitoring conductivities of liquids. More particularly, the present invention relates to an electrochemical sensor which is adapted for use in monitoring using conductimetric techniques.

2. Description of Related Art

U.S. Pat. No. 4,631,116, assigned to the present common assignee, discloses a method for monitoring the minor constituents which are present in plating bath solutions which affect plating deposit properties. The method involves applying a predetermined DC potential to a working electrode positioned within the plating bath solution. The DC potential is determined with respect to a reference electrode. A constant AC signal is superimposed on the DC potential. The DC potential is varied at a predetermined rate over a predetermined range which includes potentials which plate and strip the plating deposits.

The AC current of the applied AC signal is measured between the working electrode and a counter-electrode positioned within the plating bath solution as the DC potential is varied over the predetermined range. The measurement of the AC current in relation to varying DC potential is expressed as an AC current spectrum or fingerprint. By optimizing all AC and DC measurement variables, spectra are obtained which contain fine structure and which enable the monitoring of minor plating bath constituents which affect plating deposit properties.

For monitoring the major constituents of plating bath solutions, techniques other than the voltammetric technique described in U.S. Pat. No. 4,631,116 are needed. Commercially available conductivity measuring devices, which have been used for various laboratory and industrial process measurements, generally are not completely satisfactory for in-tank monitoring of plating bath solutions. For any measurements made in the environment of electrochemical plating baths it is necessary to provide devices having certain, desirable characteristics.

For example, in order to conduct the measurements necessary to monitor the conductivity of a plating bath solution, it is important that the electrodes of the conductivity measuring device be shielded from hydrodynamic and electrical interference from the plating bath. Further, it is important that the electrodes be positioned within the device in a manner which allows continuous and uniform passage of plating bath solution into contact with the electrodes. This requirement is necessary to ensure that the plating bath solution to which the electrodes are exposed accurately reflects overall conditions within the plating bath. In addition, a design with flexible materials of construction and inert to the generally corrosive plating bath environment is essential.

In many large scale production facilities, it would be desirable to have a rugged sensor which can withstand continual rough treatment while still providing extremely accurate measurements. The sensor should also be easily assembled and disassembled to allow cleaning and inspection. Further, the sensor should be constructed so that different electrodes may be put into the sensor to allow measurement of conductivities in many different types of liquids. In addition it would be desirable to be able to use the sensor for measuring the conductivities of solutions of widely varying concentrations.

As is apparent from the above, there presently is a need for sensor devices which are rugged enough to withstand commercial and industrial scale operations while at the same time providing for continual nonturbulent flow of solution into contact with the sensor electrodes in order to provide accurate analysis of a variety of liquids.

SUMMARY OF THE INVENTION

In accordance with the present invention, an electrochemical conductivity sensor is provided which is especially well-suited for use in the in-tank monitoring of the concentration of a wide variety of liquids, that is, a universal conductivity sensor. The sensor includes a pair of conductivity electrodes which are incorporated into a conductivity cell assembly, which is made up of a liquid flow control chamber, a sensing chamber, and a liquid exit chamber. All three of the chambers include inlets and outlets. The liquid flow control chamber outlet is connected to the sensing chamber inlet to provide for flow of the liquid being measured from the liquid flow chamber into the sensing chamber. The sensing chamber is, in turn, connected to the liquid exit chamber to provide for flow of liquid from the sensing chamber into the liquid exit chamber. In accordance with the present invention, the conductivity electrodes are located within the sensing chamber.

Liquid is transported through all three chambers by a pump. The pump transports liquid from the liquid flow control chamber inlet through the apparatus and out through the liquid exit chamber outlet. As a further feature of the present invention, a flow damper associated with the liquid flow control chamber is provided to ensure controlled hydrodynamic flow through the sensing chamber.

The electrochemical conductivity sensor in accordance with the present invention is a relatively simple and efficient device which is adapted for use in making conductivity measurements of a wide variety of liquids. The device is especially well-suited for those situations where extremely accurate measurements are required. The sensor is further well-suited for use in environments, such as plating bath solutions, wherein the solution is typically turbulent and may be corrosive. The conductivity sensor of the present invention is easily disassembled for inspection, cleaning, and replacement of electrodes. As a result, the sensor assembly may be quickly and conveniently adapted for different electrochemical measurements by disassembling the device and changing the electrodes.

As a further feature of the present invention, the chambers of the sensor are generally cylindrical in shape and made from non-conductive materials. The non-conductive materials help shield the electrodes from outside electrical disturbances. The cylindrical shape facilitates construction, increases the streamlining and durability of the sensor, and provides a strong structure for protecting the electrodes during normal abuse typically experienced in the industrial environment.

An additional feature and decided advantage of the present invention is the provision of means for adjusting the cell constant of the conductivity sensor to enable measurement of solution conductivities within various ranges. Previously used conductivity cells had a fixed geometry, hence an unchangeable cell constant, since the shape of the electrodes and the spacing between them was fixed, such as by incorporating the electrodes in glass.

The above-discussed and many other features and attendant advantages of the present invention will become better understood by reference to the following detailed description of the preferred embodiments when taken in conjunction with the accompanying drawings.

BRIEF DESCRIPTION OF THE DRAWINGS

FIG. 1 is a side view of a preferred exemplary electrochemical conductivity sensor in accordance with the present invention showing the sensor immersed in a plating bath.

FIG. 2 is a detailed side sectional view of the sensor shown in FIG. 1.

FIG. 4 is a sectional view of the sensor shown in FIG. 2 taken in the, 4—4 plane.

FIG. 5 is a sectional view of the sensor shown in FIG. 2 taken in the 5—5 plane.

FIG. 6 is a sectional view of the sensor shown in FIG. 2 taken in the 6—6 plane.

DESCRIPTION OF THE PREFERRED EMBODIMENTS

Figure 3:
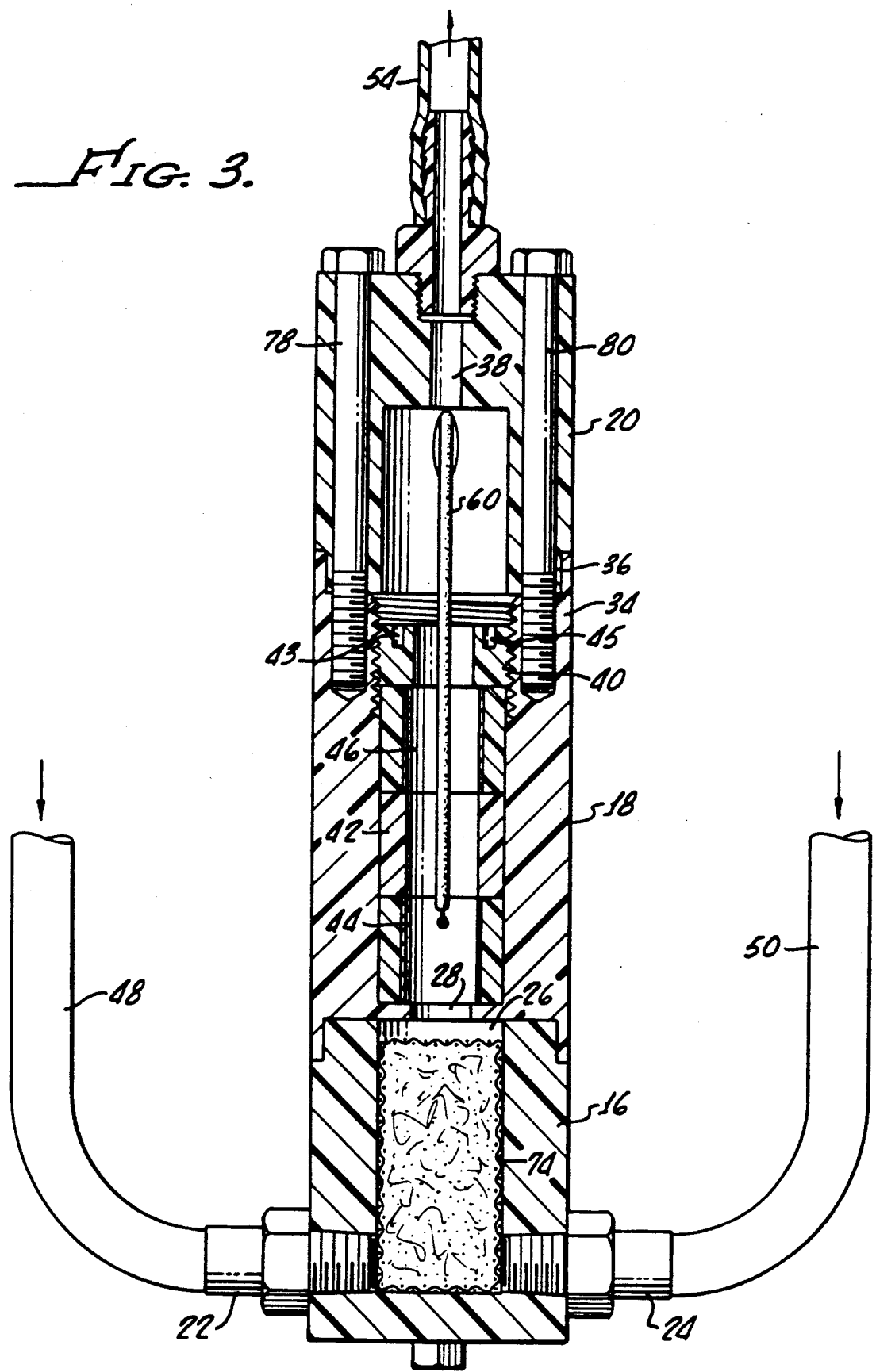
FIG. 3 is a partial side sectional view of the sensor shown in FIG, 2 taken in the 3—3 plane.

A preferred exemplary electrochemical conductivity sensor in accordance with the present invention is shown generally at 10 in FIG. 1. Sensor 10 is shown immersed in a plating bath solution 12 which is contained within a plating bath tank 14. Although sensor 10 is well-suited for use in the analysis and monitoring of plating baths, it will be understood by those skilled in the art that sensor 10 may be used to measure conductivities of a wide variety of liquids.

Sensor 10 includes a cell assembly which is made up of a liquid flow control chamber 16, a sensing chamber 18, and a liquid exit chamber 20. As best shown in FIG. 3, liquid flow control chamber 16 includes inlets 22 and 24 through which liquid enters the sensor. The liquid flow control chamber 16 also has an outlet 26 through which the liquid flows from the liquid flow control chamber 16 into the sensing chamber 18. The sensing chamber 18 includes an inlet 28 through which liquid enters the sensing chamber 18 and an outlet portion 34 through which the liquid exits the sensing chamber 18. As best shown in FIGS. 2 and 6, the liquid flow control chamber 16 is connected to the sensing chamber 18 by way of bolts 30 and 32, which are screwed into the sensing chamber as shown at 31 and 33, respectively.

The liquid exit chamber 20 includes an inlet portion 36 and an outlet portion 38 through which liquid exits the sensor 10. The sensing chamber outlet portion 34 is connected to the liquid exit chamber inlet portion 36 by way of a threaded insert 40. The threaded insert 40 engages threads on the outlet portion of the sensing chamber 34 and can be adjusted to vary the height and fix the location of sensing chamber 34.

A cell separator 42 is provided for positioning the cylindrical conductivity electrodes 44 and 46 relative to one another within the sensing chamber 18.

By changing the height of the cell separator 42 the separation between the electrodes and thus the cell constant (defined as the ratio of the gap between the electrodes to the area of the electrodes) can be varied. This feature enables the same design to be used for accurately measuring conductivity of liquids over a wide range, making the sensor more universal in use. A universal conductivity probe is thus provided according to the present invention by (1) providing a convenient means for changing electrodes and (2) providing a convenient way to substitute one cell separator for another to change the separation between the electrodes.

The threaded insert 40 includes slots 43 and 45 for accommodating a tool which can be used to raise or lower insert 40 within sensing chamber 18 (see FIG. 3).

As shown in FIG. 1, tubes 48 and 50 are connected to the inlets 22 and 24 respectively. These tubes extend upward from the inlets 22 and 24 in order to prevent bubbles from entering the liquid flow control chamber 16. In addition, the tubes 48, 50 tend to reduce the turbulence in the liquid prior to entry into the inlets 22 and 24. The length of tubes 48 and 50 will depend upon the degree of turbulence present in the plating bath solution 12. For baths which are relatively non-turbulent, the tubes 48 and 50 may be eliminated, if desired.

Referring to FIG. 1, a suction pump 52 is provided for pumping plating bath solution into the sensor 10 by suction through tubes 48 and 50, up through the sensor 10 and out through outlet 38. Pump tube 54 is used to connect the suction inlet for pump 52 to the liquid exit chamber outlet 38. Tube 56 is connected to the pump outlet and provides for the return of plating bath solution back to the tank 14. The solution is pumped only during measurements.

The walls of the liquid flow control chamber 16, sensing chamber 18 and liquid exit chamber 20 are made from a non-electrically conductive material, which is preferably a plastic, such as a polytetrafluoroethylene. Other non-conductive plastics or materials may be used provided that they are inert with respect to the particular solution in which they are to be immersed and are structurally relatively strong. The materials also should not include anything which might adversely affect the electrochemical measurements being made between the electrodes. In addition, the plastic material should be amenable to molding or machining so that the various structures required for the three chambers can be formed.

As best shown in FIGS. 2 and 3, conductivity electrodes 44 and 46 are positioned within sensing chamber 18, one above the other, separated by cell separator 42. Insulated conductivity electrode connection wires 58 and 60 pass up through the insert 40 and exit through bolts 62 and 64, which are screwed into the top of the liquid exit chamber 20 as shown at 66 and 68. O-rings 70 and 72 are provided to ensure tight seals. In addition, as best shown in FIG. 4, insulated wires 58 and 60 fit snugly within bolts 62 and 64.

The conductivity electrodes 44 and 46 are made from conventional materials typically used in electrode systems which are designed to carry typically less than 1 ampere of current and to be used in the milliivolt range, typically about 25 mv to 100 mv. Preferably they are made from platinum or other inert electrode metal which is capable of providing stable measurements. Other noble metals such as gold or palladium may also be used.

In accordance with the present invention, the liquid flow control chamber 16 may also include flow damper means such as a glass felt or screen 74. Glass felt or any other inert fibrous matrix or mesh material may be used to reduce the turbulence of liquid entering the liquid flow control chamber 16 provided that the material is capable of dampening and substantially eliminating any turbulence which may be present in the liquid entering into the sensor 10 through inlets 22 and 24. The density of the glass felt or porosity of other damping materials may be varied depending upon the size of the sensor and the degree of turbulence in the liquid as it enters the assembly through inlets 22 and 24. Preferably, the density or porosity of the damping media is sufficient to substantially eliminate any turbulence in the liquid prior to contact with the conductivity electrodes 44 and 46. At the same time, the material should not be so dense that it overly restricts the flow of liquid into the sensing chamber 18.

In operation, the sensor 10 is immersed in a plating bath or other solution to be analyzed as shown in FIG. 1. Solution is drawn into the sensor through tubes 48 and 50 by pump 52. The rate at which liquid is drawn into the sensor is limited to ensure that the turbulence dampening capabilities of the glass felt 74 are not exceeded and to ensure non-turbulent flow of liquid past the conductivity electrodes 44 and 46. The electrode wires 58 and 60 are passed out of the tank within an appropriate shielding tube 76 and connected to measurement equipment (not shown) designed for making electrochemical measurements in the millivolt range. Exemplary electrochemical analysis equipment to which the sensor of the present invention is connected may include a potentiostat and a waveform generator.

Both the exterior and interior surfaces of the liquid flow control chamber 16, sensing chamber 18 and liquid exit chamber 20 are cylindrical in shape. The cylindrical shape for the interior of the chambers is preferred because it tends to reduce the chance of turbulence being generated in the sensor as the liquid passes through the three chambers. Also, it permits using cylindrical shaped electrodes, ensuring uniform distribution, which improves stability and the accuracy of the measurements. The length of the sensor in accordance with the present invention may be varied from a few centimeters up to a meter or more depending upon the particular electrochemical properties being measured and the type of liquid being passed through the sensor. Likewise, the diameter of the sensor may be varied from 1 centimeter up to 10 centimeters or more.

The sensor 10 may be easily disassembled for cleaning, inspection or replacement of the electrodes or the cell separator by unscrewing bolts 30 and 32 and removing the liquid flow control chamber 16 from the sensing chamber 18. Next, the sensing chamber 18 and liquid exit chamber 20 can be disengaged by unscrewing bolts 78 and 80. Removing insert 40 then permits the removal of conductivity electrodes 44 and 46 and cell separator 42.

Having thus described exemplary embodiments of the present invention, it will be understood by those skilled in the art that the within disclosures are exemplary only and that the present invention is only limited by the following claims.

What is claimed is:

1. A conductivity sensor adapted for use in the conductimetric analysis of liquids, said conductivity sensor comprising:
   a liquid flow control chamber comprising an inlet and an outlet;
   a sensing chamber comprising an inlet and an outlet;
   a liquid exit chamber comprising an inlet and an outlet;
   first connection means for connecting said liquid flow control chamber outlet to said sensing chamber inlet to provide for flow of liquid from said liquid flow control chamber into said sensing chamber;
   second connection means for connecting said sensing chamber outlet to said liquid exit chamber inlet to provide for flow of liquid from said sensing chamber into said liquid exit chamber;
   a pair of conductivity electrodes located within said sensing chamber;
   means for transporting a liquid from said liquid flow control chamber inlet to said liquid exit chamber outlet; and
   flow damper means for controlling the flow of liquid through said liquid flow control chamber, so that liquid entering said sensing chamber is substantially free of turbulence.

2. A conductivity sensor according to claim 1 which further comprises:
   electrode connection means for electrically connecting said pair of conductivity electrodes to an external electrical measurement device.

3. A conductivity sensor according to claim 1 wherein said flow damper means comprises gas entry inhibitor means for preventing the entry of gas into said liquid flow control chamber.

4. A conductivity sensor according to claim 1 wherein said flow damper means comprises a mesh body located within said liquid flow control chamber through which said liquid flows as it passes through said liquid flow control chamber from said inlet to said outlet.

5. A conductivity sensor according to claim 3 wherein said flow damper means comprises a mesh body located within said liquid flow control chamber through which said liquid flows as it passes through said liquid flow control chamber from said inlet to said outlet.

6. A conductivity sensor according to claim 1 wherein said pair of conductivity electrodes are cylindrical in shape.

7. A conductivity sensor according to claim 1 wherein said sensing chamber is made from electrically non-conductive material.

8. A conductivity sensor according to claim 7 wherein said liquid flow control chamber is made from electrically non-conductive material.

9. A conductivity sensor according to claim 7 wherein said liquid exit chamber is made from electrically non-conductive material.

10. A conductivity sensor according to claim 1 wherein said liquid flow control chamber is cylindrical in shape.

11. A conductivity sensor according to claim 10 wherein said sensing chamber is cylindrical in shape.

12. A conductivity sensor according to claim 11 wherein said liquid exit chamber is cylindrical in shape.

13. A conductivity sensor according to claim 1 which further comprises means for changing the cell constant of said conductivity sensor.

14. A conductivity sensor according to claim 1 which further comprises means for changing the separation between said pair of conductivity electrodes.

15. A conductivity sensor according to claim 1 which further comprises means for changing the size of at least one of said pair of conductivity electrodes.

16. A method for measuring the conductivity of a liquid comprising the steps of:

provenance a conductivity cell assembly comprising a liquid flow control chamber, a sensing chamber and a liquid exit chamber, wherein said liquid flow control chamber comprises an inlet and an outlet, said sensing chamber comprises an inlet connected to the outlet of said liquid flow control chamber and an outlet, and said liquid exit chamber comprises an inlet connected to the outlet of said sensing chamber and an outlet;

providing a pair of conductivity electrodes within said sensing chamber;

pumping liquid through said conductivity cell assembly from said liquid flow control chamber inlet to said liquid exit chamber outlet, wherein said liquid is substantially free of turbulence as said liquid passes through said conductivity cell assembly; and determining the conductivity of said liquid between said pair of conductivity electrodes.

17. A method according to claim 16 wherein said liquid is plating bath liquid.

18. A method according to claim 16 wherein a mesh body is provided in said liquid flow control chamber to dampen any turbulence which may be present in said liquid as said liquid enters said liquid flow control chamber.

19. A method according to claim 16 wherein gas is prevented from entering said liquid flow control chamber.

20. A method according to claim 16 wherein said step of determining the conductivity of said liquid comprises the steps of:

passing an AC current through said liquid between said pair of conductivity electrodes;

measuring the AC potential across said pair of conductivity electrodes; and obtaining the conductivity of said liquid from said AC potential measurement.

21. A method according to claim 16 wherein said step of determining the conductivity of said liquid comprises the steps of:

applying an AC potential across said pair of conductivity electrodes;

measuring the AC current through said liquid between said pair of conductivity electrodes; and obtaining the conductivity of said liquid from said AC current measurement.

22. A method according to claim 16 which further comprises the steps of:

determining a range of cell constants corresponding to the range of conductivities of said liquid; and varying the separation between said pair of conductivity electrodes to provide a cell constant within said range.

23. A method according to claim 16 which further comprises the steps of:

determining a range of cell constants corresponding to the range of conductivities of said liquid; and varying the size of said pair of conductivity electrodes to provide a cell constant within said range.

* * * * *